United States Patent
Xu

(10) Patent No.: US 11,213,243 B2
(45) Date of Patent: Jan. 4, 2022

(54) METHOD FOR DETECTING QRS COMPLEX, ELECTROCARDIOGRAM DETECTION DEVICE AND READABLE STORAGE MEDIUM

(71) Applicant: Jiangyu Kangjian Innovation Medical Technology(Chengdu) Co., Ltd, Chengdu (CN)

(72) Inventor: Zhi-Bing Xu, Hangzhou (CN)

(73) Assignee: Jiangyu Kangjian Innovation Medical Technology(Chengdu) Co., Ltd, Chengdu (CN)

( * ) Notice: Subject to any disclaimer, the term of this patent is extended or adjusted under 35 U.S.C. 154(b) by 92 days.

(21) Appl. No.: 16/855,198

(22) Filed: Apr. 22, 2020

(65) Prior Publication Data
US 2021/0290095 A1  Sep. 23, 2021

(30) Foreign Application Priority Data
Mar. 23, 2020  (CN) .......................... 202010209047.4

(51) Int. Cl.
*A61B 5/00* (2006.01)
*A61B 5/366* (2021.01)
*A61B 5/316* (2021.01)
*A61B 5/352* (2021.01)

(52) U.S. Cl.
CPC .............. *A61B 5/366* (2021.01); *A61B 5/316* (2021.01); *A61B 5/352* (2021.01); *A61B 5/725* (2013.01)

(58) Field of Classification Search
CPC ............ A61B 5/366; A61B 5/346–366; A61B 5/72–7221; A61B 5/352; A61B 5/316; A61B 5/725
See application file for complete search history.

(56) References Cited

U.S. PATENT DOCUMENTS

| | | | |
|---|---|---|---|
| 2009/0216144 A1* | 8/2009 | Hopenfeld | A61B 5/349 600/521 |
| 2011/0184297 A1* | 7/2011 | Vitali | A61B 5/352 600/509 |

* cited by examiner

Primary Examiner — Scott M. Getzow
(74) Attorney, Agent, or Firm — ScienBiziP, P.C.

(57) ABSTRACT

A QRS complex detection method is provided. The method includes collecting an ECG signal and filtering the ECG signal by using at least one preset filter. The filtered ECG signal is processed using a dual-slope method. Once R wave peak is detected from the processed ECG signal, a position of a QRS complex is outputted based on the R wave peak.

20 Claims, 4 Drawing Sheets

METHOD FOR DETECTING QRS COMPLEX, ELECTROCARDIOGRAM DETECTION DEVICE AND READABLE STORAGE MEDIUM

FIELD

The present disclosure relates to medical technology, in particular to a method for detecting QRS complex, an electrocardiogram detection device and a readable storage medium.

BACKGROUND

An electrocardiogram (ECG) is an electrical activity process that reflects the excitement of a heart. ECG signal has important reference value for a study of a basic function and pathology of the heart. Generally, atypical ECG signal includes a P wave, a QRS complex, and a T wave, and a U wave may also be included. Because R wave is generally more prominent, in an analysis of the ECG signal, detection of the QRS complex is often used as a key node, which is usually a cornerstone of subsequent physiological analysis.

Since power frequency noise, EMG signals, and chip noise are basically full-band interference signals, traditional filtering methods such as low-pass, high-pass, and band-pass filters are difficult to completely filter out the full-band interference signals. In addition, an amplitude of T wave in the ECG signal is large, and may even be higher than the R wave in some populations, which is likely to cause false detection. Some research methods such as neural network algorithm, template matching algorithm, TROIKA algorithm, hidden Markov model and Hilbert-Huang transform, etc., suggest that it may not be suitable for real-time analysis because the entire ECG signals need to be processed at the same time, and the calculation-load of the ECG signals is huge.

DETAILED DESCRIPTION

In order to provide a more clear understanding of the objects, features, and advantages of the present disclosure, the same are given with reference to the drawings and specific embodiments. It should be noted that the embodiments in the present disclosure and the features in the embodiments may be combined with each other without conflict.

In the following description, numerous specific details are set forth in order to provide a full understanding of the present disclosure. The present disclosure may be practiced otherwise than as described herein. The following specific embodiments are not to limit the scope of the present disclosure.

Unless defined otherwise, all technical and scientific terms herein have the same meaning as used in the field of the art technology as generally understood. The terms used in the present disclosure are for the purposes of describing particular embodiments and are not intended to limit the present disclosure.

Figure 1:
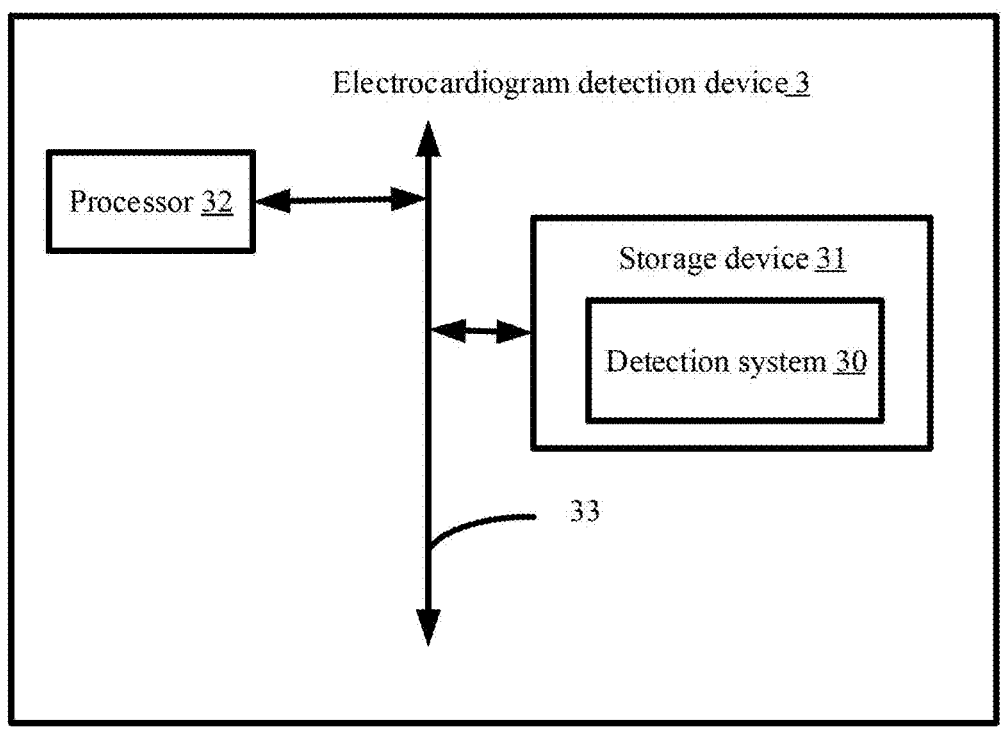
FIG. 1 illustrates a schematic diagram of an electrocardiogram detection device according to one embodiment of the present disclosure.

FIG. 1 illustrates a schematic diagram of an electrocardiogram detection device of the present disclosure.

In at least one embodiment, the electrocardiogram detection device 3 includes a storage device 31, at least one processor 32, at least one communication bus 33.

Those skilled in the art should understand that the structure of the electrocardiogram detection device 3 shown in FIG. 1 does not constitute a limitation of the embodiment of the present disclosure. The electrocardiogram detection device 3 can further include more or less other hardware or software than that shown in FIG. 1, or the electrocardiogram detection device 3 can have different component arrangements.

It should be noted that the electrocardiogram detection device 3 is merely an example. If another kind of electrocardiogram detection device can be adapted to the present disclosure, it should also be included in the protection scope of the present disclosure, and incorporated herein by reference In some embodiments, the storage device 31 may be used to store program codes and various data of computer programs. For example, the storage device 31 may be used to store a detection system 30 installed in the electrocardiogram detection device 3 and implement completion of storing programs or data during an operation of the electrocardiogram detection device 3. The storage device 31 may include Read-Only Memory (ROM), Programmable Read-Only Memory (PROM), and Erasable Programmable Read-Only Memory. EPROM), One-time Programmable Read-Only Memory (OTPROM), Electronically-Erasable Programmable Read-Only Memory (EEPROM), Compact Disc (Compact Disc) Read-Only Memory (CD-ROM) or other optical disk storage, disk storage, magnetic tape storage, or any other non-transitory computer-readable storage medium that can be used to carry or store data.

In some embodiments, the at least one processor 32 may be composed of an integrated circuit. For example, the at least one processor 32 can be composed of a single packaged integrated circuit or can be composed of multiple packaged integrated circuits with the same function or different function. The at least one processor 32 includes one or more central processing units (CPUs), one or more microprocessors, one or more digital processing chips, one or more graphics processors, and various control chips. The at least one processor 32 is a control unit of the electrocardiogram detection device 3. The at least one processor 32 uses various interfaces and lines to connect various components of the electrocardiogram detection device 3, and executes programs or modules or instructions stored in the storage device 31, and invokes data stored in the storage device 31 to perform various functions of the electrocardiogram detection device 3 and to process data, for example, perform a function of detecting QRS complex in ECG signal (for details, see the description of FIG. 3).

In some embodiments, the at least one communication bus 33 is used to implement communication connection between the storage device 31 and the at least one processor 32 and other elements of the electrocardiogram detection device 3.

In this embodiment, the detection system 30 can include one or more modules. The one or more modules are stored in the storage device 31 and are executed by at least one processor (e.g. processor 32 in this embodiment), such that a function of detecting QRS complex in ECG signal (for details, see the introduction to FIG. 3 below) is achieved.

Figure 2:
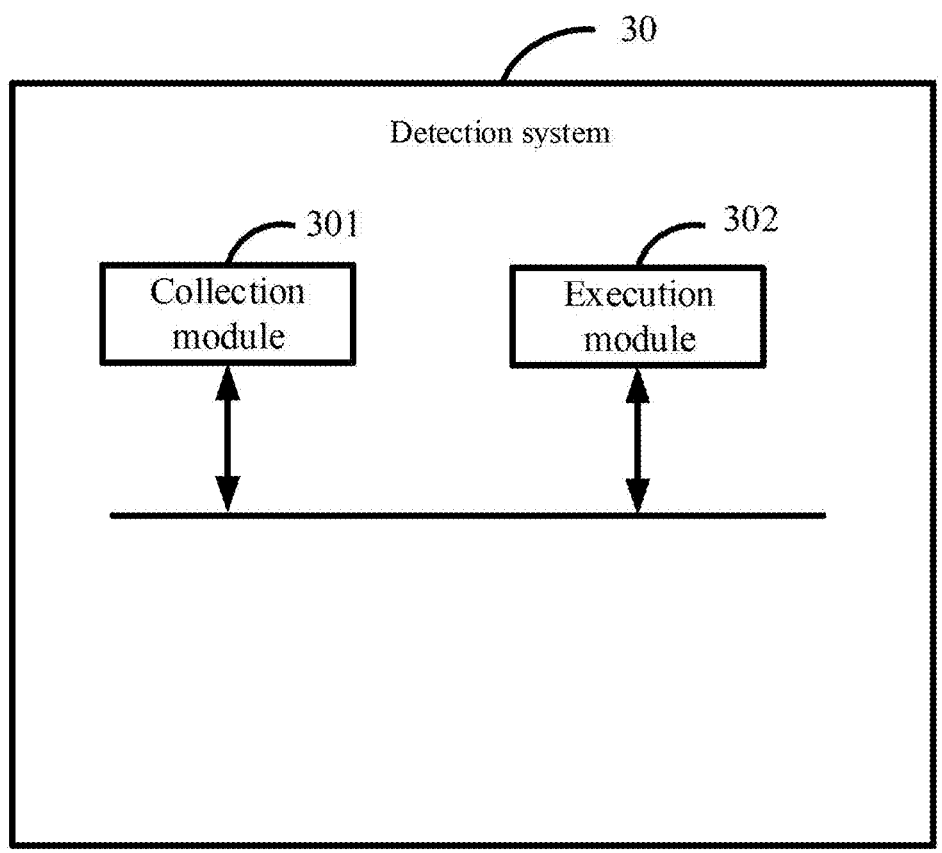
FIG. 2 shows one embodiment of modules of a detection system of the present disclosure.

In this embodiment, the detection system 30 can include a plurality of modules. Referring to FIG. 2, the plurality of modules includes a collection module 301, and an execution module 302. The module referred to in the present disclosure refers to a series of computer-readable instructions that can be executed by at least one processor (for example, the processor 32), and can complete functions, and can be stored in a storage device (for example, the storage device 31 of the electrocardiogram detection device 3). In this embodiment, functions of each module will be described in detail with reference to FIG. 3.

Figure 3:
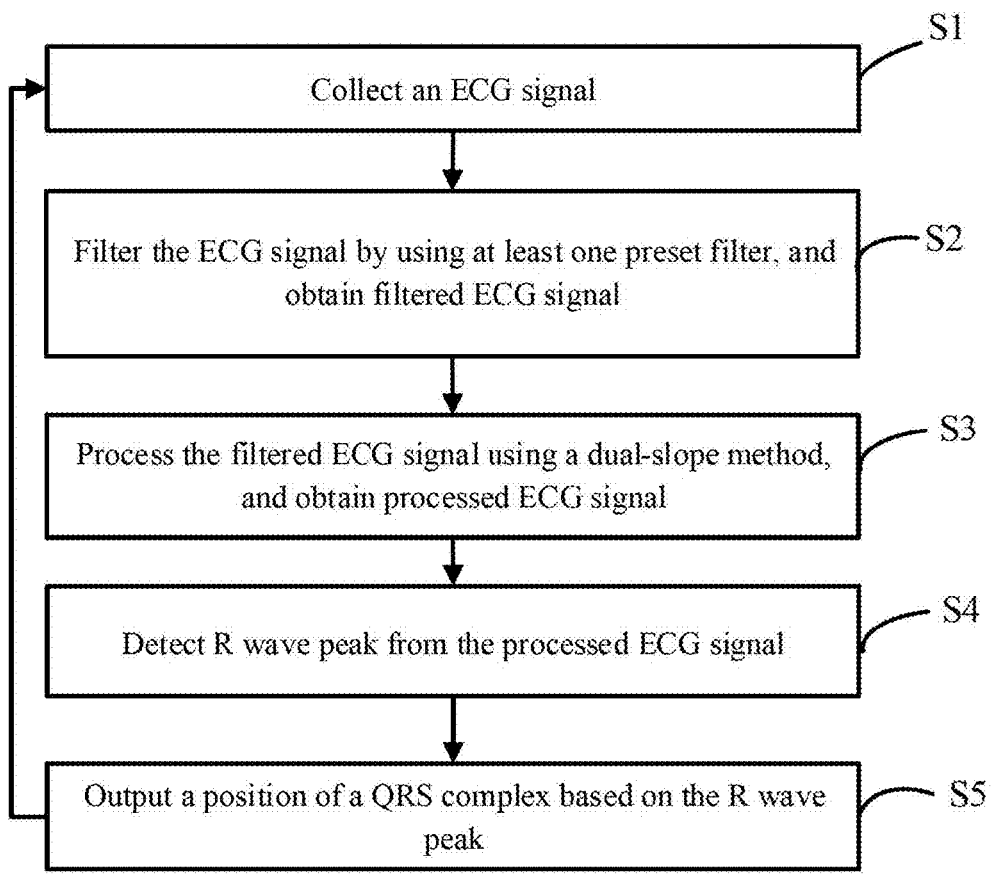
FIG. 3 shows a flow chart of one embodiment of a method for detecting QRS complex of the present disclosure.

In this embodiment, an integrated unit implemented in a form of a software module can be stored in a non-transitory readable storage medium. The above modules include one or more computer-readable instructions. The electrocardiogram detection device 3 or a processor implements the one or more computer-readable instructions, such that the method for detecting the QRS complex in the ECG signal shown in FIG. 3 is achieved.

In a further embodiment, referring to FIG. 2, the at least one processor 32 can execute an operating system of the electrocardiogram detection device 3, various types of applications (such as the detection system 30 described above), program codes, and the like.

In a further embodiment, the storage device 31 stores program codes of a computer program, and the at least one processor 32 can invoke the program codes stored in the storage device 31 to achieve related functions. For example, each module of the detection system 30 shown in FIG. 2 is program code stored in the storage device 31. Each module of the detection system 30 shown in FIG. 2 is executed by the at least one processor 32, such that the functions of the modules are achieved, and the purpose of detecting the QRS complex in ECG signal (see the description of FIG. 3 below for details) is achieved.

In one embodiment of the present disclosure, the storage device 31 stores one or more computer-readable instructions, and the one or more computer-readable instructions are executed by the at least one processor 32 to achieve a purpose of detecting QRS complex in ECG signal. Specifically, the computer-readable instructions executed by the at least one processor 32 to achieve the purpose of detecting the QRS complex in the ECG signal is described in detail in FIG. 3 below.

It should be noted that, in other embodiments, the detection system 30 may also be implemented as an embedded system with a storage device, a processor, and other necessary hardware or software.

FIG. 3 is a flowchart of a QRS complex detection method according to a preferred embodiment of the present disclosure.

In this embodiment, the QRS complex detection method can be applied to the electrocardiogram detection device 3. For the electrocardiogram detection device 3 that requires detecting QRS complex in the ECG signal, the electrocardiogram detection device 3 can be directly integrated with the function of detecting the QRS complex in the ECG signal. The electrocardiogram detection device 3 can also achieve the function of detecting the QRS complex in the ECG signal by running a Software Development Kit (SDK).

FIG. 3 shows a flow chart of one embodiment of a QRS complex detection method. Referring to FIG. 3, the method is provided by way of example, as there are a variety of ways to carry out the method. The method described below can be carried out using the configurations illustrated in FIG. 1, for example, and various elements of these figures are referenced in explanation of method. Each block shown in FIG. 3 represents one or more processes, methods, or subroutines, carried out in the method. Furthermore, the illustrated order of blocks is illustrative only and the order of the blocks can be changed. Additional blocks can be added or fewer blocks can be utilized without departing from this disclosure. The example method can begin at block S1.

At block S1, the collection module 301 collects the ECG signal.

Specifically, the collection module 301 can use electrodes attached to the skin of a human body in an area outside the heart to collect the ECG signal.

At block S2, the execution module 302 filters the collected ECG signal by using at least one preset filter, such that filtered ECG signal is obtained.

In this embodiment, the at least one preset filter can include, but is not limited to, a power frequency notch filter and a second-order infinite impulse response (IIR) high-pass filter.

In one embodiment, a frequency of the power frequency notch filter can be 50 Hz. The execution module 302 utilizes the power frequency notch filter to remove power frequency noise interference from the collected ECG signal. In one embodiment, a cutoff frequency of the second-order IIR high-pass filter can be 0.4 Hz. The execution module 302 can use the second-order IIR high-pass filter to remove baseline drift from the collected ECG signals.

In other embodiments, the at least one preset filter can be another type of filter.

At block S3, the execution module 302 processes the filtered ECG signal using a dual-slope method, and obtain processed ECG signal.

In one embodiment, the processing of the filtered ECG signal using the dual-slope method includes (a1)-(a2).

(a1) The execution module 302 calculates a maximum average slope corresponding to a left side of any one of signal sampling points of the filtered ECG signal. The execution module 302 further calculates a maximum average slope corresponding to a right side of the any one of signal sampling points.

In one embodiment, the maximum average slope corresponding to the left side of the any one of signal sampling points is $S_{L,max}$, and the maximum average slope corresponding to the right side of the any one of signal sampling points is $S_{R,max}$.

In one embodiment, $$S_{L,max} = \max\left(\frac{z_i - z_{i-k}}{k}\right),$$

$n \leq k \leq m$;

$$S_{R,max} = \max\left(\frac{z_i - z_{i+k}}{k}\right),$$

n≤k≤m, wherein "n", "m", and "k" are preset positive integers, "$z_i$" represents a voltage value of a signal sampling point "i", "$z_{i-k}$" represents a voltage value of the $k^{th}$ signal sampling point to the left from the signal sampling point "i", and "$z_{i+k}$" represents a voltage value of the $k^{th}$ signal sampling point to the right from the signal sampling point "i".

In one embodiment, the value of "n" and the value of "m" are set according to a sampling frequency of the ECG signal and a width of the QRS complex.

For example, assuming that the sampling frequency of the ECG signal is 250 Hz, and the width of the QRS complex is 0.06-0.1 s, then "n" can be equal to 6, and "m" can be equal to 15.

(a2) The execution module 302 determines a greater maximum average slope from the maximum average slope corresponding to the left side of the any one of the signal sampling points and the maximum average slope corresponding to the right side of the any one of the signal sampling points, and set the greater maximum average slope as the maximum average slope of the any one of signal sampling points.

It should be noted that, in other embodiments, when the maximum average slope corresponding to the left side of any one of signal sampling points is equal to the maximum average slope corresponding to the right side of the any one of signal sampling points, the execution module 302 can set the maximum average slope corresponding to the left side of the any one of signal sampling points or the maximum average slope corresponding to the right side of the any one of sampling points as the maximum average slope of the any one of signal sampling points.

As can be seen from FIGS. 5A-5B, after processing the filtered ECG signal using the dual-slope method, R wave peak becomes obvious and prominent, which is easier for the subsequent detection of the QRS complex.

Figure 4A:
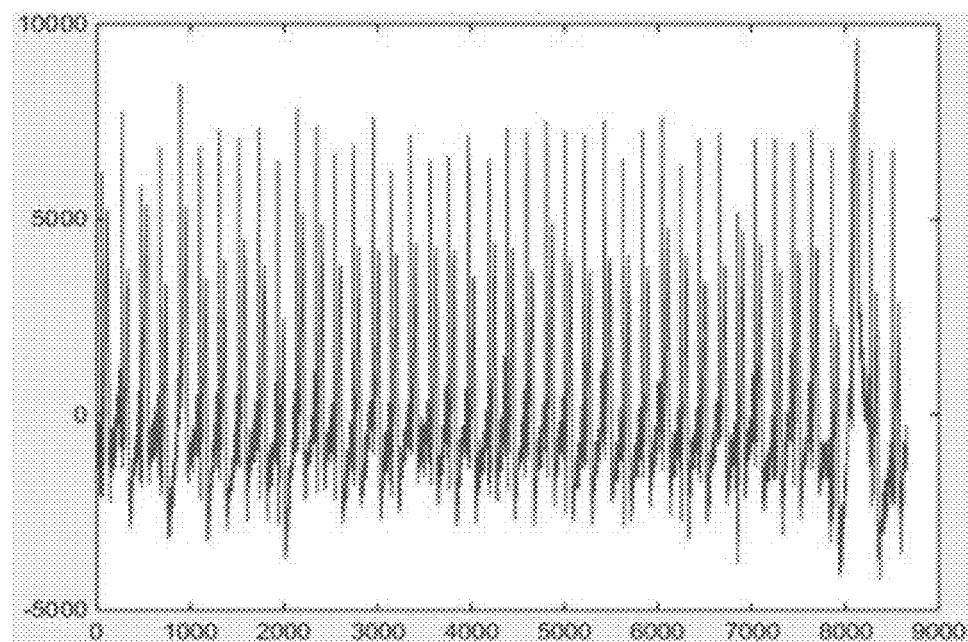
FIG. 4A illustrates a schematic diagram of the ECG signal processed by a filter.
Figure 4B:
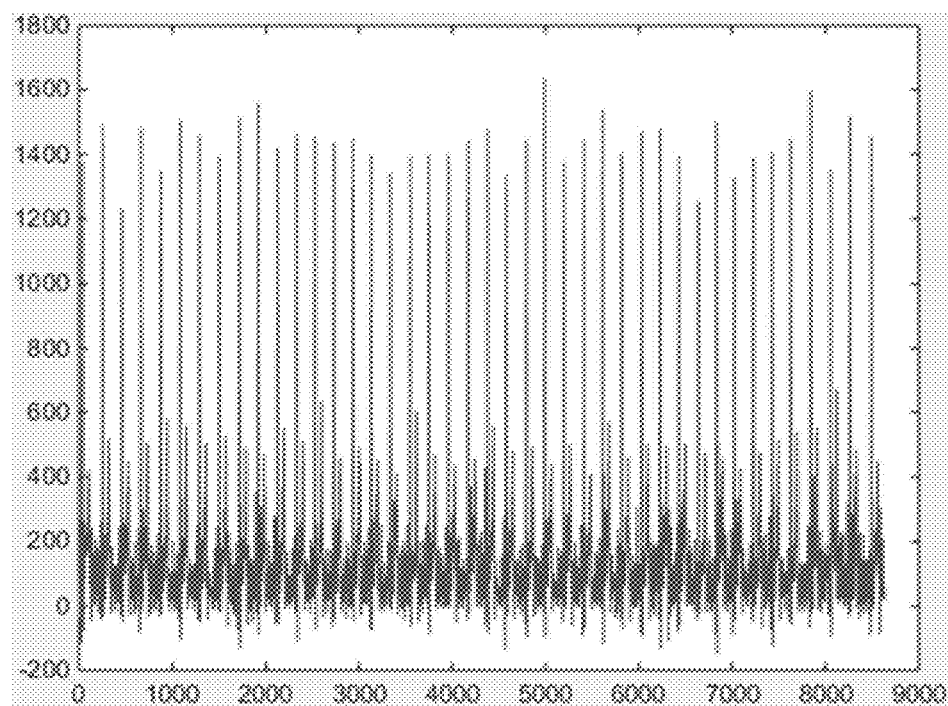
FIG. 4B illustrates a schematic diagram of the filtered ECG signal that has been processed using a dual-slope method.

Specifically, FIG. 4A is a schematic diagram of the collected ECG signal having been filtered by using the at least one preset filter. As can be seen from FIG. 4A, after the collected ECG signal is filtered, a level of the R wave peak is about 6800, a noise level is about 4300, and a noise amplitude ratio is about 63.24%. FIG. 4B is a schematic diagram of the filtered ECG signal having been processed using the dual-slope method. As can be seen from FIG. 4B, after the filtered ECG signal has been processed using the dual-slope method, the level of the R wave peak is about 1400, the noise level is about 400, and the noise amplitude ratio is about 28.57%. Obviously, after using the dual-slope method, the T wave and noise interference in the ECG signal are clearly significantly reduced. In addition, it can be seen from FIG. 4A that there is strong interference at points 8000-8500, and it can be seen from FIG. 4B that the interference at points 8000-8500 is perfectly filtered after the dual-slope method has been performed on the filtered ECG signal.

At block S4, the execution module 302 detects the R wave peak from the processed ECG signal.

In this embodiment, the detecting of the R wave peak from the processed ECG signal includes (b1)-(b2).

(b1) The execution module 302 determines whether each of the signal sampling points of the processed ECG signal is corresponding to a wave crest.

In this embodiment, the determining of whether each of the signal sampling points of the processed ECG signal is corresponding to the wave crest includes: when the voltage value of a certain signal sampling point is greater than a first threshold (to clearly describe the present disclosure, the first threshold is represented by "THR1"), and the voltage value of the certain signal sampling point is a maximum value, the execution module 302 determines that the certain signal sampling point is corresponding to the wave crest. When the voltage value of the certain signal sampling point is less than or equal to the first threshold THR1, and/or the voltage value of the certain signal sampling point is not the maximum value, the execution module 302 determines that the certain signal sampling point is not corresponding to the wave crest. The certain signal sampling point is any one of the signal sampling points of the processed ECG signal.

In other words, when the voltage value of any one of the signal sampling points is greater than the first threshold THR1, and the voltage value of the any one of the signal sampling points is the maximum value, the execution module 302 determines that the any one of the signal sampling points is corresponding to the wave crest. When the voltage value of the any one of the signal sampling points is less than or equal to the first threshold THR1, and/or the voltage value of the any one of the signal sampling points is not the maximum value, the execution module 302 determines that the any one of the signal sampling points is not corresponding to the wave crest.

In this embodiment, the voltage value of the certain signal sampling point being the maximum value means that the voltage value of the certain signal sampling point is greater than a voltage value of a previous signal sampling point and is greater than a voltage value of a next signal sampling point. The previous signal sampling point is a first signal sampling point to the left from the certain signal sampling point. The next signal sampling point is a first signal sampling point to the right from the certain signal sampling point. In other words, the voltage value of the certain signal sampling point being the maximum value means that the voltage value of the certain signal sampling point is greater than the voltage value of the first signal sampling point to the left from the certain signal sampling point, and the voltage value of the certain signal sampling point is greater than the voltage value of the first signal sampling point to the right from the certain signal sampling point.

(b2) The execution module 302 determines whether each wave crest of two adjacent wave crests is an R wave peak according to a distance between the two adjacent wave crests.

In this embodiment, the determining of whether each wave crest of the two adjacent wave crests is the R wave peak according to the distance between the two adjacent wave crests includes (b21)-(b22).

(b21) When a total number of signal sampling points between two adjacent wave crests is less than or equal to a preset value (for example, 60), the execution module 302 determines that the wave crest corresponding to a larger voltage value among the two adjacent wave crests is the R wave peak.

(b22) When the total number of signal sampling points between two adjacent wave crests is greater than the preset value, the execution module 302 determines that both of the two adjacent wave crests are R wave peaks.

At block S5, the execution module 302 outputs a position of a QRS complex based on the R wave peak.

Specifically, the position of the QRS complex can be represented by a position of the R wave peak. The position of the R wave peak can be represented by time corresponding to the signal sampling point that is corresponding to the R wave peak.

In one embodiment, the execution module 302 can output the position of the QRS complex based on a time delay of the at least one filter. For example, the execution module 302 can determine a position that the R wave peak moves backward by a preset time as the position of the QRS complex.

Specifically, the preset time can be determined according to an order of the at least one preset filter.

In other embodiments, before outputting the position of the QRS complex, the execution module 302 can adjust the first threshold THR1 and a second threshold (to clearly describe the present disclosure, the second threshold is represented by "THR2") based on a maximum peak value of peak values of all R wave peaks currently detected based on the following formula. The second threshold THR2 is used to determine the first threshold THR1.

Specifically, $$THR1 = \begin{cases} 0.125 \times \frac{\text{peak}}{4} + 0.875 \times THR1, & \text{if}(\text{peak} > THR2) \\ \frac{0.4 \times \text{peak} + THR1}{2}, & \text{else} \end{cases};$$

$$THR2 = \begin{cases} 0.125 \times 0.7 \times \text{peak} + 0.875 \times THR1, & \text{if}(\text{peak} > THR2) \\ THR2 - \frac{\text{peak} - THR2}{2}, & \text{else} \end{cases},$$

wherein "peak" represents the maximum peak value.

It should be noted that because the execution module 302 can adjust the first threshold value THR1 and the second threshold value THR2 in real time based on the maximum peak value of the peak values of all R wave peaks, such that the present disclosure can adapt to signal levels changing in real time, and can effectively abovid non-detection of the R wave peak and false detections of the R wave peak, such that a detection sensitivity and a detection accuracy are improved.

The above description is only embodiments of the present disclosure, and is not intended to limit the present disclosure, and various modifications and changes can be made to the present disclosure. Any modifications, equivalent substitutions, improvements, etc. made within the spirit and scope of the present disclosure are intended to be included within the scope of the present disclosure.

What is claimed is:

1. A QRS complex detection method applied to an electrocardiogram detection device, the method comprising:
   collecting an ECG signal;
   filtering the ECG signal by using at least one preset filter, and obtaining filtered ECG signal;
   processing the filtered ECG signal using a dual-slope method, and obtaining processed ECG signal;
   detecting R wave peak from the processed ECG signal; and
   outputting a position of a QRS complex based on the R wave peak.

2. The QRS complex detection method according to claim 1, wherein the at least one preset filter comprises a power frequency notch filter and a second-order infinite impulse response (IIR) high-pass filter.

3. The QRS complex detection method according to claim 1, wherein the processing of the filtered ECG signal using a dual-slope method comprises:
   calculating a maximum average slope corresponding to a left side of any one of signal sampling points of the filtered ECG signal;
   calculating a maximum average slope corresponding to a right side of the any one of signal sampling points;
   determining a greater maximum average slope from the maximum average slope corresponding to the left side of the any one of the signal sampling points and the maximum average slope corresponding to the right side of the any one of the signal sampling points, and setting the greater maximum average slope as the maximum average slope of the any one of signal sampling points.

4. The QRS complex detection method according to claim 3, wherein the maximum average slope corresponding to the left side of the any one of signal sampling points is $S_{L,max}$, and the maximum average slope corresponding to the right side of the any one of signal sampling points is $S_{R,max}$; wherein $$S_{L,max} = \max\left(\frac{z_i - z_{i-k}}{k}\right),$$

$n \leq k \leq m$;

$$S_{R,max} = \max\left(\frac{z_i - z_{i+k}}{k}\right),$$

$n \leq k \leq m$, wherein "n", "m", and "k" are preset positive integers, "$z_i$" represents a voltage value of a signal sampling point "i", "$z_{i-k}$" represents a voltage value of the $k^{th}$ signal sampling point to the left from the signal sampling point "i", and "$z_{i+k}$" represents a voltage value of the $k^{th}$ signal sampling point to the right from the signal sampling point "i".

5. The QRS complex detection method according to claim 4, wherein the detecting of R wave peak from the processed ECG signal comprises:
   determining whether each of the signal sampling points of the processed ECG signal is corresponding to a wave crest; and
   determining whether each wave crest of two adjacent wave crests is an R wave peak according to a distance between the two adjacent wave crests.

6. The QRS complex detection method according to claim 5, wherein the determining of whether each of the signal sampling points of the processed ECG signal is corresponding to the wave crest comprises:
   determining a certain signal sampling point is corresponding to the wave crest when the voltage value of the certain signal sampling point is greater than a first threshold THR1, and the voltage value of the certain signal sampling point is a maximum value, wherein the certain signal sampling point is any one of the signal sampling points of the processed ECG signal; and
   determining the certain signal sampling point is not corresponding to the wave crest when the voltage value of the certain signal sampling point is less than or equal to the first threshold THR1, and/or the voltage value of the certain signal sampling point is not the maximum value;
   wherein the determining of whether each wave crest of two adjacent wave crests is the R wave peak according to the distance between the two adjacent wave crests comprises:
   determining the wave crest corresponding to a larger voltage value among the two adjacent wave crests is the R wave peak, when a total number of signal sampling points between the two adjacent wave crests is less than or equal to a preset value; and determining both of the two adjacent wave crests are R wave peaks when the total number of signal sampling points between the two adjacent wave crests is greater than the preset value.

7. The QRS complex detection method according to claim 6, further comprising:
adjusting the first threshold THR1 and a second threshold THR2 based on a maximum peak value of peak values of all R wave peaks currently detected based on following formula, wherein the second threshold THR2 is used to determine the first threshold THR1;

$$THR1 = \begin{cases} 0.125 \times \frac{\text{peak}}{4} + 0.875 \times THR1, & \text{if(peak} > THR2) \\ \frac{0.4 \times \text{peak} + THR1}{2}, & \text{else} \end{cases} ;$$

$$THR2 = \begin{cases} 0.125 \times 0.7 \times \text{peak} + 0.875 \times THR1, & \text{if(peak} > THR2) \\ THR2 - \frac{\text{peak} - THR2}{2}, & \text{else} \end{cases} ,$$

wherein the maximum peak value is represented using "peak".

8. An electrocardiogram detection device comprising:
a storage device;
at least one processor; and
the storage device storing one or more programs, which when executed by the at least one processor, cause the at least one processor to:
collect an ECG signal;
filter the ECG signal by using at least one preset filter, and obtain filtered ECG signal;
process the filtered ECG signal using a dual-slope method, and obtain processed ECG signal;
detect R wave peak from the processed ECG signal; and
output a position of a QRS complex based on the R wave peak.

9. The electrocardiogram detection device according to claim 8, wherein the at least one preset filter comprises a power frequency notch filter and a second-order infinite impulse response (IIR) high-pass filter.

10. The electrocardiogram detection device according to claim 8, wherein the processing of the filtered ECG signal using a dual-slope method comprises:
calculating a maximum average slope corresponding to a left side of any one of signal sampling points of the filtered ECG signal;
calculating a maximum average slope corresponding to a right side of the any one of signal sampling points;
determining a greater maximum average slope from the maximum average slope corresponding to the left side of the any one of the signal sampling points and the maximum average slope corresponding to the right side of the any one of the signal sampling points, and setting the greater maximum average slope as the maximum average slope of the any one of signal sampling points.

11. The electrocardiogram detection device according to claim 10, wherein the maximum average slope corresponding to the left side of the any one of signal sampling points is $S_{L,max}$, and the maximum average slope corresponding to the right side of the any one of signal sampling points is $S_{R,max}$; wherein $$S_{L,max} = \max\left(\frac{z_i - z_{i-k}}{k}\right),$$

$n \leq k \leq m$;

$$S_{R,max} = \max\left(\frac{z_i - z_{i+k}}{k}\right),$$

$n \leq k \leq m$,
wherein "n", "m", and "k" are preset positive integers, "$z_i$" represents a voltage value of a signal sampling point "i", "$z_{i-k}$" represents a voltage value of the $k^{th}$ signal sampling point to the left from the signal sampling point "i", and "$z_{i+k}$" represents a voltage value of the $k^{th}$ signal sampling point to the right from the signal sampling point "i".

12. The electrocardiogram detection device according to claim 11, wherein the detecting of R wave peak from the processed ECG signal comprises:
determining whether each of the signal sampling points of the processed ECG signal is corresponding to a wave crest; and
determining whether each wave crest of two adjacent wave crests is an R wave peak according to a distance between the two adjacent wave crests.

13. The electrocardiogram detection device according to claim 12, wherein the determining of whether each of the signal sampling points of the processed ECG signal is corresponding to the wave crest comprises:
determining a certain signal sampling point is corresponding to the wave crest when the voltage value of the certain signal sampling point is greater than a first threshold THR1, and the voltage value of the certain signal sampling point is a maximum value, wherein the certain signal sampling point is any one of the signal sampling points of the processed ECG signal; and
determining the certain signal sampling point is not corresponding to the wave crest when the voltage value of the certain signal sampling point is less than or equal to the first threshold THR1, and/or the voltage value of the certain signal sampling point is not the maximum value;
wherein the determining of whether each wave crest of two adjacent wave crests is the R wave peak according to the distance between the two adjacent wave crests comprises:
determining the wave crest corresponding to a larger voltage value among the two adjacent wave crests is the R wave peak, when a total number of signal sampling points between the two adjacent wave crests is less than or equal to a preset value; and
determining both of the two adjacent wave crests are R wave peaks when the total number of signal sampling points between the two adjacent wave crests is greater than the preset value.

14. The electrocardiogram detection device according to claim 13, wherein the at least one processor is further caused to:
adjust the first threshold THR1 and a second threshold THR2 based on a maximum peak value of peak values of all R wave peaks currently detected based on following formula, wherein the second threshold THR2 is used to determine the first threshold THR1;

$$THR1 = \begin{cases} 0.125 \times \frac{\text{peak}}{4} + 0.875 \times THR1, & \text{if(peak} > THR2) \\ \frac{0.4 \times \text{peak} + THR1}{2}, & \text{else} \end{cases} ;$$

-continued $$THR2 = \begin{cases} 0.125 \times 0.7 \times peak + 0.875 \times THR1, & \text{if}(peak > THR2) \\ THR2 - \frac{peak - THR2}{2}, & \text{else} \end{cases},$$

wherein the maximum peak value is represented using "peak".

15. A non-transitory storage medium having instructions stored thereon, when the instructions are executed by a processor of an electrocardiogram detection device, the processor is configured to perform a QRS complex detection method, wherein the method comprises:
 collecting an ECG signal;
 filtering the ECG signal by using at least one preset filter, and obtaining filtered ECG signal;
 processing the filtered ECG signal using a dual-slope method, and obtaining processed ECG signal;
 detecting R wave peak from the processed ECG signal; and
 outputting a position of a QRS complex based on the R wave peak.

16. The non-transitory storage medium according to claim 15, wherein the processing of the filtered ECG signal using a dual-slope method comprises:
 calculating a maximum average slope corresponding to a left side of any one of signal sampling points of the filtered ECG signal;
 calculating a maximum average slope corresponding to a right side of the any one of signal sampling points;
 determining a greater maximum average slope from the maximum average slope corresponding to the left side of the any one of the signal sampling points and the maximum average slope corresponding to the right side of the any one of the signal sampling points, and setting the greater maximum average slope as the maximum average slope of the any one of signal sampling points.

17. The non-transitory storage medium according to claim 16, wherein the maximum average slope corresponding to the left side of the any one of signal sampling points is $S_{L,max}$, and the maximum average slope corresponding to the right side of the any one of signal sampling points is $S_{R,max}$; wherein $$S_{L,max} = \max\left(\frac{z_i - z_{i-k}}{k}\right),$$

$n \le k \le m$;

$$S_{R,max} = \max\left(\frac{z_i - z_{i+k}}{k}\right),$$

$n \le k \le m$,
wherein "n", "m", and "k" are preset positive integers, "$z_i$" represents a voltage value of a signal sampling point "i", "$z_{i-k}$" represents a voltage value of the $k^{th}$ signal sampling point to the left from the signal sampling point "i", and "$z_{i+k}$" represents a voltage value of the $k^{th}$ signal sampling point to the right from the signal sampling point "i".

18. The non-transitory storage medium according to claim 17, wherein the detecting of R wave peak from the processed ECG signal comprises:
 determining whether each of the signal sampling points of the processed ECG signal is corresponding to a wave crest; and
 determining whether each wave crest of two adjacent wave crests is an R wave peak according to a distance between the two adjacent wave crests.

19. The non-transitory storage medium according to claim 18, wherein the determining of whether each of the signal sampling points of the processed ECG signal is corresponding to the wave crest comprises:
 determining a certain signal sampling point is corresponding to the wave crest when the voltage value of the certain signal sampling point is greater than a first threshold THR1, and the voltage value of the certain signal sampling point is a maximum value, wherein the certain signal sampling point is any one of the signal sampling points of the processed ECG signal; and
 determining the certain signal sampling point is not corresponding to the wave crest when the voltage value of the certain signal sampling point is less than or equal to the first threshold THR1, and/or the voltage value of the certain signal sampling point is not the maximum value;
 wherein the determining of whether each wave crest of two adjacent wave crests is the R wave peak according to the distance between the two adjacent wave crests comprises:
 determining the wave crest corresponding to a larger voltage value among the two adjacent wave crests is the R wave peak, when a total number of signal sampling points between the two adjacent wave crests is less than or equal to a preset value; and
 determining both of the two adjacent wave crests are R wave peaks when the total number of signal sampling points between the two adjacent wave crests is greater than the preset value.

20. The non-transitory storage medium according to claim 19, wherein the method further comprises:
 adjusting the first threshold THR1 and a second threshold THR2 based on a maximum peak value of peak values of all R wave peaks currently detected based on following formula, wherein the second threshold THR2 is used to determine the first threshold THR1;

$$THR1 = \begin{cases} 0.125 \times \frac{peak}{4} + 0.875 \times THR1, & \text{if}(peak > THR2) \\ \frac{0.4 \times peak + THR1}{2}, & \text{else} \end{cases};$$

$$THR2 = \begin{cases} 0.125 \times 0.7 \times peak + 0.875 \times THR1, & \text{if}(peak > THR2) \\ THR2 - \frac{peak - THR2}{2}, & \text{else} \end{cases},$$

wherein the maximum peak value is represented using "peak".

* * * * *